US007119197B2

(12) United States Patent
Learmonth

(10) Patent No.: US 7,119,197 B2
(45) Date of Patent: Oct. 10, 2006

(54) METHOD FOR PREPARATION OF (S)-(+)-AND(R)-(-)10,11-DIHYDRO-10-HYDRODOXY-5H-DIBENZ/B,F/AZEPHINE-5-CARBOXAMIDE

(75) Inventor: David Alexander Learmonth, Maia (PT)

(73) Assignee: Portela & C.A., S.A., (PT)

( * ) Notice: Subject to any disclaimer, the term of this patent is extended or adjusted under 35 U.S.C. 154(b) by 242 days.

(21) Appl. No.: 10/477,371

(22) PCT Filed: May 10, 2002

(86) PCT No.: PCT/GB02/02176

§ 371 (c)(1),
(2), (4) Date: Apr. 9, 2004

(87) PCT Pub. No.: WO02/092572

PCT Pub. Date: Nov. 21, 2002

(65) Prior Publication Data

US 2004/0162280 A1 Aug. 19, 2004

(30) Foreign Application Priority Data

May 11, 2001 (GB) ................................ 0111566.6

(51) Int. Cl.
*C07D 223/28* (2006.01)

(52) U.S. Cl. ...................................................... 540/589

(58) Field of Classification Search ................ 540/589
See application file for complete search history.

(56) References Cited

U.S. PATENT DOCUMENTS 5,451,687 A 9/1995 Sato et al. .................. 549/253

FOREIGN PATENT DOCUMENTS

| | | |
|---|---|---|
| EP | 0751129 | 1/1997 |
| JP | 10087536 | 4/1998 |
| JP | 10139732 | 5/1998 |
| WO | WO97/01742 | 1/1997 |

OTHER PUBLICATIONS

Jan Benes et al.: "Anticonvulsant and sodium channel-blocking properties of novel 10, 11-Dihydro-5H-dibenz(b,f)azephine-5-caboxamide derivatives", J. Med. Chem., Am. Chem. Soc., vol. 42, 1999, pp. 2582-2587, XP002206156.

*Primary Examiner*—Brenda Coleman
(74) *Attorney, Agent, or Firm*—Rankin, Hill, Porter & Clark LLP

(57) ABSTRACT

An efficient and high-yielding method for the preparation of optically pure (S)-(+) -10,11-dihydro-10-hydroxy-5H-dibenz/b,f/azepine-5-carboxamide and (R)-(−)-10,11-dihydro-10-hydroxy-5H-dibenz/b,f/azepine-5-carboxamide by resolution of racemic (±)-10,11-dihydro-10-hydroxy-5H-dibenz/b,f/azepine-5-carboxamide using a tartaric acid anhydride.

20 Claims, No Drawings

METHOD FOR PREPARATION OF (S)-(+)-AND(R)-(-)10,11-DIHYDRO-10-HYDRODOXY-5H-DIBENZ/B,F/AZEPHINE-5-CARBOXAMIDE

This invention relates to a method for the preparation of (S)-(+)- and (R)-(−)-10,11-dihydro-10-hydroxy-5H-dibenz/b,f/azepine-5-carboxamide.

In recent years, a significant change in the way that chiral compounds are viewed within the pharmaceutical industry has been witnessed. Beforehand, many molecules containing asymmetric centres were launched onto the drug marketplace as racemic mixtures. Subsequent concerns as to the safety and/or efficacy of such racemic drugs has persuaded the industry to research and develop single stereoisomer drugs. These concerns were based on the concept that racemic drugs could be considered to be 50% impure, since one isomer of a given racemic mixture is often pharmacologically inactive or significantly less active than the other isomer; indeed, one isomer may exert a different action or give origin to unwanted side-effects. Isomeric compounds may undergo different metabolic processes which complicates pharmacokinetic issues further. Consequently, drug regulatory authorities have become increasingly more cautious and frequently demand concise information on the properties and behaviour of individual isomers.

A particularly interesting example in this respect is the case of oxcarbazepine (OXC), the 10-keto analogue of carbamazepine (CBZ). These two compounds are structurally very similar and are currently used in the treatment of epilepsy. Oxcarbazepine was designed to avoid the oxidative metabolic transformation of CBZ and is claimed to be a better tolerated drug (Grant, S. M. et al., Drugs, 43, 873–888 (1992)). However oxcarbazepine undergoes rapid and complete metabolism in vivo to the racemic 10-hydroxy derivative of oxcarbazepine, called “MHD” (see (±)-MHD, Schutz, H. et al., Xenobiotica, 16(8), 769–778 (1986)) and therefore represents an apparently achiral drug which undergoes metabolic transformation to give a mixture of two pharmacologically active enantiomers.

The synthesis and improved anticonvulsant properties of (S)-(−)-10-acetoxy-10,11-dihydro-5H-dibenz/b,f/azepine-5-carboxamide (BIA 2-093), and (R)-(+)-10-acetoxy-10,11-dihydro-5H-dibenz/b,f/azepine-5-carboxamide (BIA 2-059), both single-isomer drugs specifically designed to avoid such formation of racemic mixtures of active metabolites have been described (Benes, J. et al., U.S. Pat. No. 5,753,646 and Benes, J. et al., J. Med. Chem., 42, 2582–2587 (1999)). The key step of the synthesis of compounds BIA 2-093 and BIA 2-059 involves the resolution of racemic 10,11-dihydro-10-hydroxy-5H-dibenz/b,f/azepine-5-carboxamide ((±)-MHD) into its separate, optically pure stereoisomers, (S)-(+)-10,11-dihydro-10-hydroxy-5H-dibenz/b,f/azepine-5-carboxamide ((S)-(+)-MHD), and (R)-(−)-10,11-dihydro-10-hydroxy-5H-dibenz/b,f/azepine-5-carboxamide ((R)-(−)-MHD), which are the principal intermediates.

Both stereoisomers of MHD are known compounds and are commonly used as standards in studies of oxcarbazepine metabolism. The resolution of the racemic alcohol has been previously described in the chemical literature (Benes, J. et al., J. Med. Chem., 42, 2582–2587 (1999) and Volosov, A. et al., Epilepsia, 41(9), 1107–1111 (2000)). These methods involve the formation of diasteroisomeric menthoxyacetate-ester derivatives of (±)-MHD; by taking advantage of the different solubilities of these diasteroisomeric esters, separation is possible by fractional crystallisation and subsequent hydrolysis affords the individually pure stereoisomers, (S)-(+)-MHD and (R)-(−)-MHD. However, this method was utilised for the preparation of only rather small quantities of each stereoisomer and contains certain inherent disadvantages which preclude its use for the preparation of pilot-scale quantities and thereafter industrial production. The necessary optically pure resolving agents, (+) and (−)-menthoxyacetic acid are extremely expensive and are not readily available in sufficiently large quantities from commercial sources. Their preparation from cheaper, readily available optically pure (+) or (−)-menthol could be considered, but this preparation is tedious, slow and potentially dangerous. Furthermore, these menthoxyacetic acids require ‘activation’ in order to react with (±)-MHD and form the key intermediate diastereoisomeric menthoxyacetate esters. This activation is normally achieved via conversion of the free acids to the acid chlorides (these acid chlorides are again very expensive products from commercial sources), an extra synthetic step which requires the use of unpleasant halogenating reagents such as for example thionyl chloride or oxalyl chloride. Alternatively, this reaction can be accomplished using a coupling reagent such as for example dicyclohexylcarbodiimide. This reagent is also expensive; additionally it is difficult to manipulate due to its low melting point and is indicated as a potent skin irritant, thus posing health risks for workers. Often there are encountered difficulties in removing completely the dicyclohexylurea by-product from the wanted product. A further and very serious limitation of this method is the relatively low yield obtained of the optically pure menthoxyacetate ester which is isolated after crystallisation, in yields usually only marginally better than 20% (the maximum yield being 50% for each isomer).

There is lacking therefore in the prior art, a safe, economical, scaleable and efficient (high-yielding) method useful for the preparation of (S)-(+)-10,11-dihydro-10-hydroxy-5H-dibenz/b,f/azepine-5-carboxamide and (R)-(−)-10,11-dihydro-10-hydroxy-5H-dibenz/b,f/azepine-5-carboxamide.

It is an object of the invention to provide an improved method for the preparation of (S)-(+)-10,11-dihydro-10-hydroxy-5H-dibenz/b,f/azepine-5-carboxamide and (R)-(−)-10,11-dihydro-10-hydroxy-5H-dibenz/b,f/azepine-5-carboxamide. A further object of the invention is to provide a method which avoids the disadvantages of the prior art.

We have now found that is it possible to separate the stereoisomers of (S)-(+)-MHD and (R)-(−)-MHD) from the racemic mixture by means of an efficient and high yielding process which involves the use of an appropriate tartaric acid anhydride to resolve the stereoisomers. In particular we have found that the (2R,3R)-di-O,O'-substituted-tartartic acid anhydride can be used to precipitate the diastereoisomeric precursor of (S)-(+)-MHD, and the (2S,3S)-di-O,O'-substituted-tartaric acid anhydride can be used to precipitate the diastereoisomeric precursor of (R)-(−)-MHD.

According to one aspect of the invention there is provided a method for the preparation of optically pure (S)-(+)-10,11-dihydro-10-hydroxy-5H-dibenz/b,f/azepine-5-carboxamide, comprising the steps of:

(1) reacting racemic (±)-10,11-dihydro-10-hydroxy-5H-dibenz/b,f/azepine-5-carboxamide with (2R,3R)-di-O,O'-substituted-tartaric acid anhydride to give a separable mixture of diastereoisomeric 10-O-di-O,O'-substituted-tartrate half-esters of (±)-10,11-dihydro-10-hydroxy-5H-dibenz/b,f/azepine-5-carboxamide;

(2) precipitation of the less soluble diastereoisomeric 10-O-di-O,O'-substituted-tartrate half-ester formed in step (1) by addition of water and separation of the same, preferably by filtration; and (3) hydrolysis of the less soluble diastereoisomeric 10-O-di-O,O'-substituted-tartrate half-ester obtained in step (2), preferably catalysed with a base, to give the optically pure (S)-(+)-10,11-dihydro-10-hydroxy-5H-dibenz/b,f/azepine-5-carboxamide.

According to another aspect of the invention there is provided a method for the preparation of optically pure (R)-(−)-10,11-dihydro-10-hydroxy-5H-dibenz/b,f/azepine-5-carboxamide, comprising the steps of:

(1) reacting racemic (±)-10,11-dihydro-10-hydroxy-5H-dibenz/b,f/azepine-5-carboxamide with (2S,3S)-di-O,O'-substituted-tartaric acid anhydride to give a separable mixture of diastereoisomeric 10-O-di-O,O'-substituted-tartrate half-esters;

(2) precipitation of the less soluble diastereoisomeric 10-O-di-O,O'-substituted-tartrate half-ester formed in step (1) by addition of water and separation of the same, preferably by filtration; and (3) hydrolysis of the less soluble 10-O-di-O,O'-substituted-tartrate half-ester obtained in step (2), preferably catalysed with a base, to give the optically pure (R)-(−)-10,11-dihydro-10-hydroxy-5H-dibenz/b,f/azepine-5-carboxamide.

More specifically, the invention relates to a method for the preparation of (S)-(+)-10,11-dihydro-10-hydroxy-5H-dibenz/b,f/azepine-5-carboxamide and (R)-(−)-10,11-dihydro-10-hydroxy-5H-dibenz/b,f/azepine-5-carboxamide by resolution of racemic (±)-10,11-dihydro-10-hydroxy-5H-dibenz/b,f/azepine-5-carboxamide via the eight steps indicated below (which should be read in conjunction with the reaction scheme set out herein below):

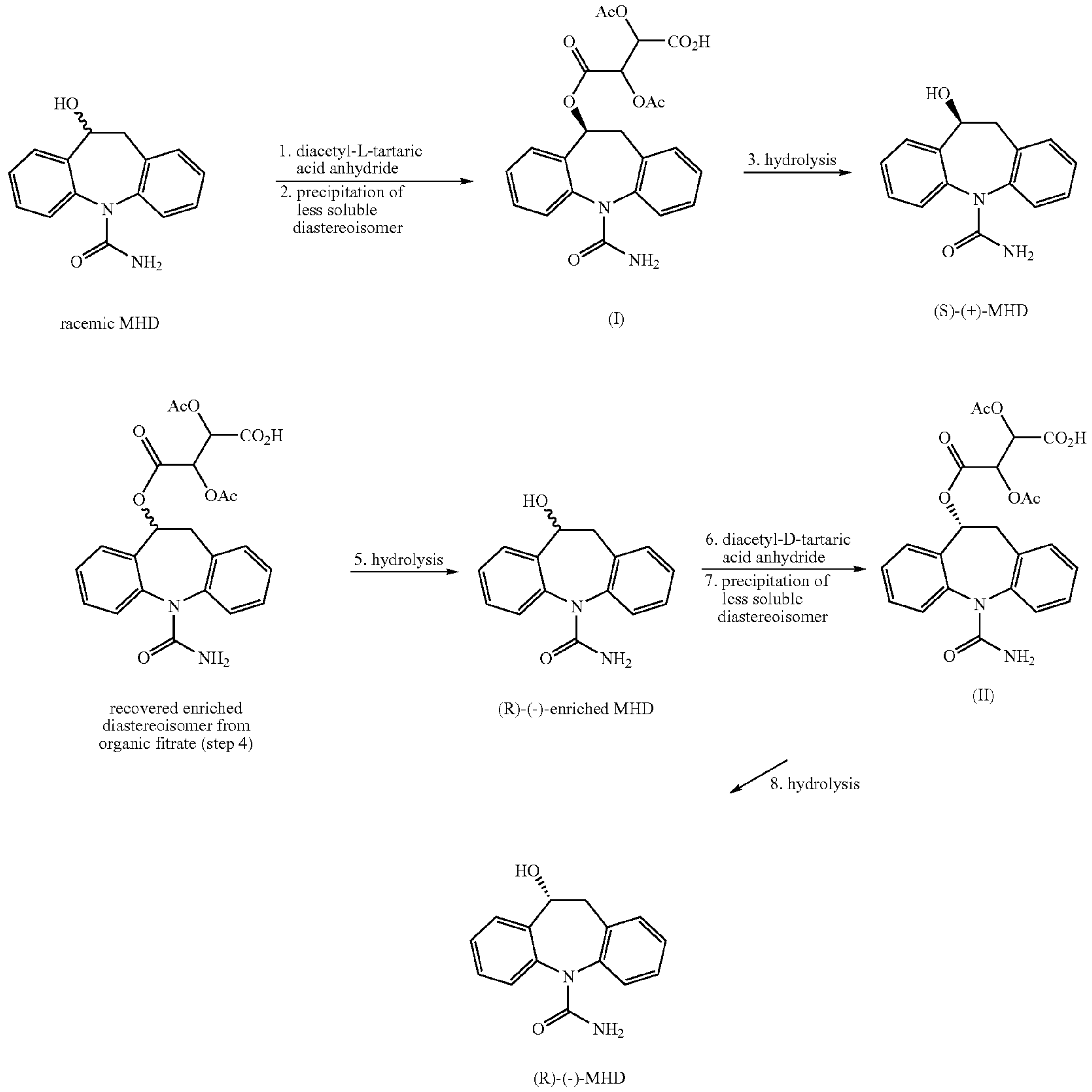

(1) reacting racemic (±)-10,11-dihydro-10-hydroxy-5H-dibenz/b,f/azepine-5-carboxamide with a di-O,O'-substituted-L-tartaric acid anhydride such as (2R,3R)-di-O,O'-acetyltartaric acid anhydride to give a mixture (substantially 50:50) of diastereoisomeric diacetyl tartrate half-esters (2) precipitation of the less soluble diastereoisomeric diacetyl tartrate half-ester (I) formed in step (1) and separation by filtration (3) base-catalysed hydrolysis of the diacetyl tartrate half-ester obtained in step (2) to give optically pure (S)-(+)-10,11-dihydro-10-hydroxy-5H-dibenz/b,f/azepine-5-carboxamide (4) recovery from the organic filtrate from step (2) of the more-soluble diastereoisomeric diacetyl tartrate half-ester (5) base-catalysed hydrolysis of the more-soluble diastereoisomeric diacetyl tartrate half-ester from step (4) to give enriched (R)-(−)-10,11-dihydro-10-hydroxy-5H-dibenz/b,f/azepine-5-carboxamide (6) reaction of the enriched (R)-(−)-10,11-dihydro-10-hydroxy-5H -dibenz/b,f/azepine-5-carboxamide from step (5) with a di-O,O'-substituted-D-tartaric acid anhydride such as (2S,3S)-di-O,O'-acetyltartaric acid anhydride to give a mixture of diastereoisomeric diacetyl tartrate half-esters.

(7) precipitation of the less soluble diastereoisomeric diacetyl tartrate half-ester (II) formed in step (6) and separation by filtration (8) base-catalysed hydrolysis of the diacetyl tartrate half-ester obtained in step (7) to give optically pure (R)-(−)-10,11-dihydro-10-hydroxy-5H-dibenz/b,f/azepine-5-carboxamide Step (1) utilises (2R,3R)-di-O,O'-substituted-tartaric acid anhydride and step (6) utilises (2S,3S)-di-O,O'-substituted-tartaric acid anhydride for preparation of the diastereoisomeric half-esters by acylation of (±)-MHD. It is possible to change the order of the reaction steps so that the (R)-(−)-10,11-dihydro-10-hydroxy-5H-dibenz/b,f/azepine-5-carboxamide is produced first, followed by the (S)-(+)-10,11-dihydro-10-hydroxy-5H-dibenz/b,f/azepine-5-carboxamide In the present invention, the -di-O,O'-substituted-tartaric acid anhydrides have the following structural formula:

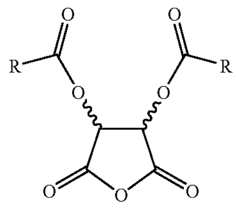

where each R is the same and is $C_1$ to $C_6$ alkyl, most preferably methyl, or each R is phenyl.

We prefer that the tartaric acid anhydride is either (2R,3R)di-O,O'-acetyltartaric acid anhydride and its antipode (2S,3S)-di-O,O'-acetyltartaric acid anhydride; or (2R,3R)-di-O,O'-benzoyltartaric acid anhydride or its antipode (2S,3S)-di-O,O'-benzoyltartaric acid anhydride.

These tartaric acid anhydrides are known compounds and can be easily prepared from tartaric acid, for example, by the reaction of cheap and readily available L-(+)-tartaric or D-(−)-tartaric acid respectively with acetic anhydride under sulphuric acid catalysis (Shriner, R. L. et al., Organic Synthesis, Collective Volume 4, 242–243). The use of these compounds as resolving agents has been described in an unrelated process (Varkonyi-Schlovicsko, E. et al., RO 100033 B1 and J. Heterocycl. Chem., 34(3), 1065–1066 (1997)).

The reactions in steps (1) and (6) are preferably carried out by stirring the racemic alcohol with a small excess of the appropriate tartaric acid anhydride (1.1–1.2 molar equivalents) in the presence of an organic base such as pyridine or triethylamine in a substantially inert solvent, preferably a chlorinated hydrocarbon solvent such as dichloromethane. The reaction is carried out preferably at room temperature and when the reaction is complete (around one hour), water is added to the reaction mixture. The mixture may then be stirred at room temperature for a period of 12–18 hours, during which time there occurs precipitation of the less soluble diastereoisomeric diacetyl tartrate half-ester (step (2)). The precipitate is filtered off and is preferably washed with water (see further description below) and dried to afford the pure diastereoisomeric diacetyl tartrate half-ester in high chemical yields. The hydrolysis of the pure diastereoisomeric diacetyl tartrate half-ester (step (3)) may be achieved by stirring in an alcoholic solvent such as for example, methanol and addition of an excess of inorganic base such as sodium or potassium hydroxide, preferably as a dilute (2–3N) aqueous solution (steps (5) and (8) are carried out similarly). The reaction is carried out preferably at room temperature, and when complete, the precipitated sodium bitartrate is easily removed by filtration and may be recycled if desired. Water is preferably added to the residue and the mixture is allowed to stand for a period of 16–24 hours, during which time the optically pure alcohol crystallises from the mixture. The product is removed by filtration and washed with excess water. After drying, there is obtained either the optically pure (S)-(+)- or (R)-(−)-antipode of 10,11-dihydro-10-hydroxy-5H-dibenz/b,f/azepine-5-carboxamide, depending on the optical form of the tartaric acid used. Further smaller amounts of almost optically pure alcohol may be recovered from the filtrate by extraction with organic solvent(s), such as dichloromethane or a dichloromethane/isopropanol mixture in which the alcohol is soluble. If desired, the combined crops of the alcohol may be recrystallised from a warm alcoholic solvent such as for example, ethanol, isopropanol or from ethyl acetate or the alcohol can be recrystallised from mixtures of one of these solvents with a chlorinated solvent such as dichloromethane. On standing for a period of 16–24 hours, the optically pure alcohol is collected by filtration and after drying, is obtained in chemical yields within the range of 80–90%. The optical purity of the product may be assessed by polarimetry or by HPLC using a chiral column for analysis. The alcohols obtained by this method have optical purity in the range 92% to 98% or 99%. In this specification the expression "optically pure" includes compounds which have optical purity in the range 92–98%, and preferably 92–99%.

At the point described above where the precipitate is filtered off and preferably washed with water, the organic phase of the filtrate may be separated and the aqueous phase may be extracted with an organic solvent such as dichloromethane. The organic solvent may then be dried over anhydrous sodium sulphate and evaporated by distillation, preferably under reduced pressure to leave a residue which consists mainly of the opposite diastereoisomeric diacetyl tartrate half-ester (step (4)), which can then be hydrolysed (step 5) and subsequently treated by the same sequence as described in the above process using the corresponding optically pure tartaric acid anhydride resolving reagent (steps 6–8) to eventually provide the corresponding optically pure alcohol antipode.

According to another aspect of the invention there is provided a method for the preparation of a compound of the formula III:

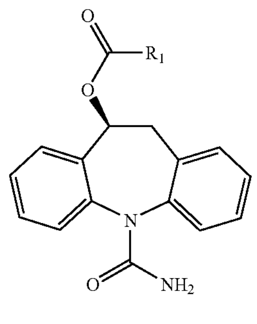

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromin or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming (S)-(+)-10,11-dihydro-10-hydroxy-5H-dibenz/b,f/azepine-5-carboxamide by a method as described above, then treating the (S)-(+)-10,11-dihydro-10-hydroxy-5H-dibenz/b,f/azepine-5-carboxamide to produce the compound of formula III. The compound of formula I is preferably prepared by acylating the (S)-(+)-10,11-dihydro-10-hydroxy-5H-dibenz/b,f/azepine-5-carboxamide.

According to another aspect of the invention there is provided a method for the preparation of a compound of the formula IV:

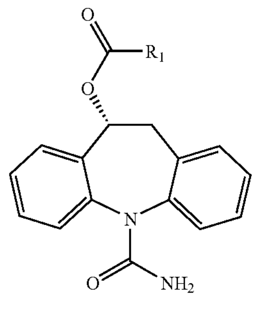

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromin or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming (R)-(−)-10,11-dihydro-10-hydroxy-5H-dibenz/b,f/azepine-5-carboxamide by a method as described above, then treating the (R)-(−)-10,11-dihydro-10-hydroxy-5H-dibenz/b,f/azepine-5-carboxamide to produce the compound of formula IV. The compound of formula II is preferably prepared by acylating the (R)-(−)-10,11-dihydro-10-hydroxy-5H-dibenz/b,f/azepine-5-carboxamide.

The compounds of formulas III and IV are described in more detail in our U.S. Pat. No. 5,753,646, the contents of which are incorporated herein by reference. The method can be used to produce optically pure stereoisomers of any of the compounds disclosed in U.S. Pat. No. 5,753,646. For example, to produce (S)-(+)-10-acetoxy-10,11-dihydro-5H-dibenz/b,f/azepine-5-carboxamide it is possible to add acetylchloride in dichloromethane to a suspension of (S)-(+)-10,11-dihydro-10-hydroxy-5H-dibenz/b,f/azepine-5-carboxamide and pyridine in dichloromethane, as described in example 4, of U.S. Pat. No. 5,753,646.

The (S)-(+)- and (R)-(−)-stereoisomers of the compounds described in examples 4 to 17 of U.S. Pat. No. 5,753,646 can be produced by acylation using the appropriate acyl halide. The compounds described in examples 18 to 23 can be produced using the appropriate carboxylic acid.

Using the present invention it is therefore possible to produce the (S)-(+)- and (R)-(−)-stereoisomers of the following compounds:

(1) 10-acetoxy-10,11-dihydro-5H-dibenz/b,f/azepine-5-carboxamide
(2) 10-benzoyloxy-10,11-dihydro-5H-dibenz/b,f/azepine-5-carboxamide
(3) 10-(4-methoxybenzoyloxy)-10,11-dihydro-5H-dibenz/b,f/azepine-5-carboxamide
(4) 10-(3-methoxybenzoyloxy)-10,11-dihydro-5H-dibenz/b,f/azepine-5-carboxamide
(5) 10-(2-methoxybenzoloxy)-10,11-dihydro-5H-dibenz/b,f/azepine-5-carboxamide
(6) 10-(4-nitrobenzoyloxy)-10,11-dihydro-5H-dibenz/b,f/azepine-5-carboxamide
(7) 10-(3-nitrobenzoyloxy)-10,11-dihydro-5H-dibenz/b,f/azepine-5-carboxamide
(8) 10-(2-nitrobenzoyloxy)-10,11-dihydro-5H-dibenz/b,f/azepine-5-carboxamide
(9) 10-(4-chlorobenzoyloxy)-10,11-dihydro-5H-dibenz/b,f/azepine-5-carboxamide
(10) 10-(3-chlorobenzoyloxy)-10,11-dihydro-5H-dibenz/b,f/azepine-5-carboxamide
(11) 10-(2-acetoxybenzoyloxy)-10,11-dihydro-5H-dibenz/b,f/azepine-5-carboxamide
(12) 10-propionyloxy-10,11-dihydro-5H-dibenz/b,f/azepine-5-carboxamide
(13) 10-butyryloxy-10,1-dihydro-5H-dibenz/b,f/azepine-5-carboxamide
(14) 10-pivaloyloxy-10,11-dihydro-5H-dibenz/b,f/azepine-5-carboxamide
(15) 10-[(2-propyl) pentanoyloxy]-10,11-dihydro-5H-dibenz/b,f/azepine-5-carboxamide
(16) 10-[(2-ethyl)hexanoyloxy]-10,11-dihydro-5H-dibenz/b,f/azepine-5-carboxamide
(17) 10-stearoyloxy-10,11-dihydro-5H-dibenz/b,f/azepine-5-carboxamide
(18) 10-cyclopentanoyloxy-10,11-dihydro-5H-dibenz/b,f/azepine-5-carboxamide
(19) 10-cyclohexanoyloxy-10,11-dihydro-5H-dibenz/b,f/azepine-5-carboxamide1
(20) 10-phenylacetoxy-10,11-dihydro-5H-bibenz/b,f/azepine-5-carboxamide
(21) 10-(4-methoxyphenyl)acetoxy-10,11-dihydro-5H-dibenz/b,f/-azepine-5-carboxamide
(22) 10-(3-methoxyphenyl)acetoxy-10,11-dihydro-5H-dibenz/b,f/azepine-5-carboxamide
(23) 10-(4-nitrophenyl)acetoxy-10,11-dihydro-5H-dibenz/b,f/azepine-5-carboxamide
(24) 10-(3-nitrophenyl)acetoxy-10,11-dihydro-5H-dibenz/b,f/azepine-5-carboxamide

(25) 10-nicotinoyloxy-10,11-dihydro-5H-dibenz/b,f/azepine-5-carboxamide

(26) 10-isonicotinoyloxy-10,11-dihydro-5H-dibenz/b,f/azepine-5-carboxamide

(27) 10-chloroacetoxy-10,11-dihydro-5H-dibenz/b,f/azepine-5-carboxamide

(28) 10-bromoacetoxy-10,11-dihydro-5H-dibenz/b,f/azepine-5-carboxamide

(29) 10-formyloxy-10,11-dihydro-5H-dibenz/b,f/azepine-5-carboxamide

(30) 10-ethoxycarbonyloxy-10,11-dihydro-5H-dibenz/b,f/azepine-5-carboxamide

(31) 10-(2-chloropropionyloxy)-10,11-dihydro-5H-dibenz/b,f/azepine-5-carboxamide These compounds, or pharmaceutically acceptably derivatives thereof (such as salts), can be used in the preparation of pharmaceutical compositions comprising the compound itself, or the derivative, in combination with a pharmaceutically acceptable carrier. Such compositions have anticonvulsant properties and can be used in the treatment of some central and peripheric nervous system disorders, such as epilepsy.

According to another aspect of the invention there is provided a compound of formula V:

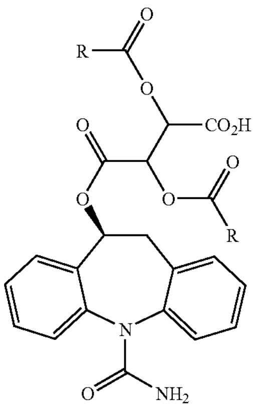

where each R is $C_1$ to $C_6$ alkyl (preferably methyl), or each R is phenyl.

According to another aspect of the invention there is provided a compound of formula VI:

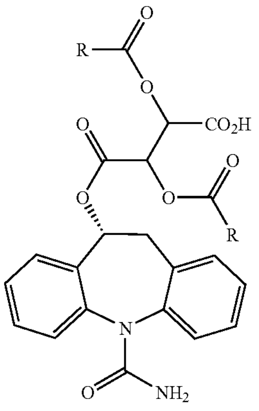

where each R is $C_1$ to $C_6$ alkyl (preferably methyl), or each R is phenyl.

The invention disclosed herein is exemplified by the following examples of preparation. It is to be understood that the invention is not to be limited to the exact details of operation as obvious modifications and equivalents will be apparent to those skilled in the art.

EXAMPLE 1 racemic (±)-10,11-dihydro-10-hydroxy-5H-dibenz/b,f/azepine-5-carboxamide

To a stirred suspension of oxcarbazepine (10,11-dihydro-10-oxo-5H-dibenz/b,f/azepine-5-carboxamide) (172.0 g, 0.682 mol) in a mixture of 96% ethanol (700 mL) and water (400 mL) at room temperature was added portionwise sodium borohydride (20.0 g, 0.529 mol) over ten minutes, causing foaming of the reaction mixture. After stirring at 45° C. for one hour there was added acetone (150 mL) cautiously. The reaction mixture was then evaporated (40° C., water aspirator pressure) to a residual volume of around 500 mL. Water (2000 mL) was added to the semi-solid residue with stirring and the reaction mixture was stored at 5° C. for sixteen hours. The crystalline product was filtered, washed with water (1000 mL) and dried to constant weight to give racemic (±)-10,11-dihydro-10-hydroxy-5H-dibenz/b,f/azepine-5-carboxamide (157.8 g, 91%) of m.p. 185–188° C.

EXAMPLE 2

(S)-(+)-10,11-dihydro-10-hydroxy-5H-dibenz/b,f/azepine-5-carboxamide

L-(+)-Tartaric acid (36.0 g, 0.24 mol) was stirred with acetic anhydride (95.3 g, 0.933 mol) at room temperature and two drops of sulphuric acid (96%) were added. After two minutes, an exothermic reaction started and the temperature rose to 80° C. The reaction mixture was then heated at reflux for ten minutes, whereupon the volatile components were removed by evaporation (70° C., water aspirator pressure). To the remaining semi-crystalline mass was added toluene (50 mL) and the evaporation was repeated under the same conditions. Further toluene (50 ml) was added to the residue followed by evaporation under the same conditions.

To the resulting semi-crystalline residue (approximately 52.0 g) was added dichloromethane (500 mL) followed by racemic (±)-10,11-dihydro-10-hydroxy-5H-dibenz/b,f/azepine-5-carboxamide (50.8 g, 0.2 mol), pyridine (17.5 g, 0.221 mol) and 4-dimethylaminopyridine (1.0 g, 0.008 mol). The reaction mixture was stirred at room temperature for forty minutes whereupon water (350 mL) was added and the resulting light-brown solution was stirred for twelve hours at 18° C. The precipitated solid was filtered off, washed with water (5×50 mL) and dried until constant weight to afford the intermediate crystalline diastereoisomeric diacetyl tartrate half-ester (I) (46.03 g, 98% based on one diastereoisomer) of m.p. 228–229° C. ($[\alpha]_D^{20}$=−37° (c=1, pyridine)). The filtrate was subsequently used for the preparation of (R)-(−)-MHD (Example 3).

To a stirred suspension of this diacetyl tartrate half-ester (46.0 g, 0.098 mol) in methanol (270 mL) at room temperature was added aqueous sodium hydroxide solution (3N, 133 mL, 0.4 mol) and the resulting mixture was stirred for thirty minutes, whereupon the precipitated sodium bitartrate was filtered off and washed with methanol (40 mL). The methanol was removed from the combined filtrate by evaporation (45° C., water aspirator pressure) and water (400 mL) was added to the residue. After standing at 18° C. for sixteen hours, the crystalline product was filtered off, washed with water (2×50 mL) and dried to constant weight to afford a white solid (21.73 g, 87.4%). The combined filtrates were extracted with 10% isopropanol/dichloromethane solution; the organic extracts were washed by brine (100 mL), dried over anhydrous sodium sulphate and filtered. Evaporation of the solvents (40° C., water aspirator pressure) afforded a further crop of the same product (2.14 g, 8.6%). The combined crops were dissolved in hot ethanol (115 mL) and left to stand at 5° C. for sixteen hours. The crystalline product was filtered off, washed with cold ethanol (25 mL) and dried to constant weight to give (S)-(+)-10,11-dihydro-10-hydroxy-5H-dibenz/b,f/azepine-5-carboxamide (20.90 g, 84%) of m.p. 187–189° C. ($[\alpha]_D^{20}$=189° (c=1, pyridine), corresponding to 96% optical purity, confirmed by chiral HPLC) (LiChroCART 250-4 HPLC Cartridge ChiraDex 5 μm, (Merck), Flow: 0.75 mL/min, Mobile Phase: 0.1M aqueous solution $Na_2HPO_4$/methanol 8:2 (pH=7.0), Sample 10 μmL of 0.2 mg analyte/mL of mobile phase, UV detection at 254 nm, retention time of (S)-(+)-alcohol 9.60 min).

EXAMPLE 3

(R)-(−)-10,11-dihydro-10-hydroxy-5H-dibenz/b,f/azepine-5-carboxamide

The filtrate from Example 2 was separated and the phases were separated. The aqueous phase was extracted by 10% isopropanol/dichloromethane solution and the combined organic phases were washed by brine (100 mL), dried over anhydrous sodium sulphate and filtered. Evaporation of the solvent (40° C., water aspirator pressure) gave a residue consisting mainly of the opposite optically impure diastereoisomeric diacetyl tartrate half-ester (approximately 48.0 g).

To a stirred suspension of this optically impure diacetyl tartrate half-ester (48.0 g, 0.102 mol) in methanol (280 mL) at room temperature was added aqueous sodium hydroxide solution (3N, 139 mL, 0.42 mol) and the resulting mixture was stirred for thirty minutes, whereupon the precipitated sodium bitartrate was filtered off and washed with methanol (40 mL). The methanol was removed from the combined filtrate by evaporation (45° C., water aspirator pressure) and water (350 mL) was added to the residue. After standing at 18° C. for sixteen hours, the crystalline product was filtered off, washed with water (2×50 mL) and dried to constant weight to afford a white solid (21.9 g, 84%). The combined filtrates were extracted with 10% isopropanol/dichloromethane solution; the organic extracts were washed by brine (100 mL), dried over anhydrous sodium sulphate and filtered. Evaporation of the solvents (40° C., water aspirator pressure) afforded a further crop of the same product (2.98 g, 11.5%). The two crops were combined to give enriched (R)-(−)-10,11-dihydro-10-hydroxy-5H-dibenz/b,f/azepine-5-carboxamide (24.88 g, 96%).

D-(−)-Tartaric acid (17.57 g, 0.117 mol) was stirred with acetic anhydride (46.5 g, 0.455 mol) at room temperature and two drops of sulphuric acid (96%) were added. After two minutes, an exothermic reaction started and the temperature rose to 80° C. The reaction mixture was then heated at reflux for ten minutes, whereupon the volatile components were removed by evaporation (70° C., water aspirator pressure). To the remaining semi-crystalline mass was added toluene (50 mL) and the evaporation was repeated under the same conditions. Further toluene (50 ml) was added to the residue followed by evaporation under the same conditions.

To the resulting semi-crystalline residue (approximately 26 g) was added dichloromethane (250 mL) followed by (R)-(−)-enriched 10,11-dihydro-10-hydroxy-5H-dibenz/b,f/azepine-5-carboxamide (24.8 g, 0.098 mol), pyridine (8.54 g, 0.108 mol) and 4-dimethylaminopyridine (0.5 g, 0.004 mol). The reaction mixture was stirred at room temperature for forty minutes whereupon water (180 mL) was added and the resulting light-brown solution was stirred for twelve hours at 18° C. The precipitated solid was filtered off, washed with water (5×30 mL) and dried until constant weight to afford the intermediate crystalline diastereoisomeric diacetyl tartrate half-ester (II) (37.21 g, 81%) of m.p. 228–229° C. ($[\alpha]_D^{20}$=42° (c=1, pyridine)).

To a stirred suspension of this half-ester (37.0 g, 0.079 mol) in methanol (220 mL) at room temperature was added aqueous sodium hydroxide solution (3N, 107 mL, 0.323 mol) and the resulting mixture was stirred for thirty minutes, whereupon the precipitated sodium bitartrate was filtered off and washed with methanol (30 mL). The methanol was removed from the combined filtrate by evaporation (45° C., water aspirator pressure) and water (270 mL) was added to the residue. After standing at 18° C. for sixteen hours, the crystalline product was filtered off, washed with water (2×30 mL) and dried to constant weight to afford a white solid (17.79 g, 89%). The combined filtrates were extracted with 10% isopropanol/dichloromethane solution; the organic extracts were washed by brine (100 mL), dried over anhydrous sodium sulphate and filtered. Evaporation of the solvents (40° C., water aspirator pressure) afforded a further crop of the same product (0.72 g, 3.6%). The combined crops were dissolved in hot ethanol (70 mL) and left to stand at 5° C. for sixteen hours. The crystalline product was filtered off, washed with cold ethanol (10 mL) and dried to constant weight to give (R)-(−)-10,11-dihydro-10-hydroxy-5H-dibenz/b,f/azepine-5-carboxamide (17.84 g, 89%) of m.p. 187–189° C. ($[\alpha]_D^{20}$=−193° (c=1, pyridine), corresponding to 98% optical purity, confirmed by chiral HPLC) (LiChroCART 250-4 HPLC Cartridge ChiraDex 5 μm, (Merck), Flow: 0.75 mL/min, Mobile Phase: 0.1M aqueous solution $Na_2HPO_4$/methanol 8:2 (pH=7.0), Sample 10 μmL of 0.2 mg analyte/mL of mobile phase, UV detection at 254 nm, retention time of (R)-(−)-alcohol 8.74 min).

It will be appreciated that the invention described above may be modified.

What is claimed is:

1. A method for the preparation of optically pure (S)-(+)-10,11-dihydro-10-hydroxy-5H-dibenz[b,f]azepine-5-carboxamide, the method comprising the steps of:

(1) reacting racemic (±)-10,11-dihydro-10-hydroxy-5H-dibenz[b,f]azepine-5-carboxamide with (2R,3R)-di-O,O'-substituted-tartaric acid anhydride to give a separable mixture (1:1) of diastereoisomeric 10-O-di-O,O'-substituted-tartrate half-esters of (±)-10,11-dihydro-10-hydroxy-5H -dibenz[b,f]azepine-5-carboxamide;

(2) precipitation of the less soluble diastereoisomeric 10-O-di-O,O'-substituted-tartrate half-ester formed in step (1) by addition of water and separation of the same by filtration; and (3) base-catalysed hydrolysis of the less soluble diastereoisomeric 10-O-di-O,O'-substituted-tartrate half-ester obtained in step (2) to give the optically pure (S)-(+)-10,11-dihydro-10-hydroxy-5H-dibenz[b,f]azepine-5-carboxamide, wherein the (2R,3R)-di-O,O'-substituted-tartaric acid anhydride has the formula:

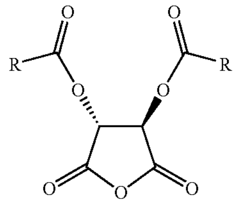

where each R is the same and is $C_1$ to $C_6$ alkyl, or each R is phenyl.

2. A method for the preparation of optically pure (R)-(−)-10,11-dihydro-10-hydroxy-5H-dibenz[b,f]azepine-5-carboxamide, the method comprising the steps of:

(1) reacting racemic (±)-10,11-dihydro-10-hydroxy-5H-dibenz[b,f]azepine-5-carboxamide with (2S,3S)-di-O,O'-substituted-tartaric acid anhydride to give a separable mixture of diastereoisomeric 10-O-di-O,O'-substituted-tartrate half-esters;

(2) precipitation of the less soluble diastereoisomeric 10-O-di-O,O'-substituted-tartrate half-ester formed in step (1) by addition of water and separation of the same by filtration; and (3) base-catalysed hydrolysis of the less soluble 10-O-di-O,O'-substituted-tartrate half-ester obtained in step (2) to give the optically pure (R)-(−)-10,11-dihydro-10-hydroxy-5H-dibenz[b,f]azepine-5-carboxamide, wherein the (2S,3S)-di-O,O'-substituted-tartaric acid anhydride has the formula:

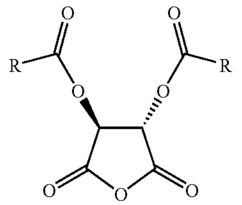

where each R is the same and is $C_1$ to $C_6$ alkyl, or each R is phenyl.

3. A method for the preparation of optically pure (S)-(+)-10,11-dihydro-10-hydroxy-5H-dibenz[b,f]azepine-5-carboxamide and (R)-(−)-10,11-dihydro-10-hydroxy-5H-dibenz[b,f]azepine-5-carboxamide, the method comprising the steps of:

(1) reacting racemic (±)-10,11-dihydro-10-hydroxy-5H-dibenz[b,f]azepine-5-carboxamide with (2R,3R)-di-O,O'-substituted-tartaric acid anhydride to give a separable mixture (1:1) of diastereoisomeric 10-O-di-O,O'-substituted-tartrate half-esters of (±)-10,11-dihydro-10-hydroxy-5H-dibenz[b,f]azepine-5-carboxamide;

(2) precipitation of the less soluble diastereoisomeric 10-O-di-O,O'-substituted-tartrate half-ester formed in step (1) by addition of water and separation of the same by filtration;

(3) base-catalysed hydrolysis of the less soluble diastereoisomeric 10-O-di-O,O'-substituted-tartrate half-ester obtained in step (2) to give the optically pure (S)-(+)-10,11-dihydro-10-hydroxy-5H-dibenz[b,f]azepine-5-carboxamide;

(4) recovery from the organic filtrate from step (2) of the more-soluble diastereoisomeric 10-O-di-O,O'-substituted-tartrate half-ester;

(5) base-catalysed hydrolysis of the recovered, more-soluble diastereoisomeric 10-O-di-O,O'-substituted-tartrate half-ester from step (4) to give enriched (R)-(−)-10,11-dihydro-10-hydroxy-5H-dibenz[b,f]azepine-5-carboxamide;

(6) reaction of enriched (R)-(−)-10,11-dihydro-10-hydroxy-5H-dibenz[b,f]azepine-5-carboxamide from step (5) with (2S,3S)-di-O,O'-substituted-tartaric acid anhydride to give a separable mixture of diastereoisomeric 10-O-di-O,O'-substituted-tartrate half-esters;

(7) precipitation of the less soluble diastereoisomeric 10-O-di-O,O'-substituted-tartrate half-ester formed in step (6) by addition of water and separation of the same by filtration; and (8) base-catalysed hydrolysis of the less soluble 10-O-di-O,O'-substituted-tartrate half-ester obtained in step (7) to give the optically pure (R)-(−)-10,11-dihydro-10-hydroxy-5H-dibenz[b,f]azepine-5-carboxamide, wherein the (2R,3R)-di-O,O'-substituted-tartaric acid anhydride has the formula:

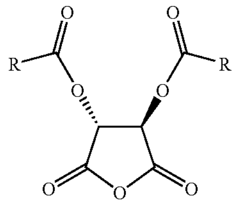

where each R is the same and is $C_1$ to $C_6$ alkyl, or each R is phenyl, and wherein the (2S,3S)-di-O,O'-substituted-tartaric acid anhydride has the formula:

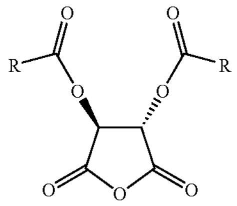

where each R is the same and is $C_1$ to $C_6$ alkyl, or each R is phenyl.

4. A method for the preparation of optically pure (S)-(+)-10,11-dihydro-10-hydroxy-5H-dibenz[b,f]azepine-5-carboxamide and (R)-(−)-10,11-dihydro-10-hydroxy-5H-dibenz[b,f]azepine-5-carboxamide, the method comprising the steps of:

(1) reacting racemic (±)-10,11-dihydro-10-hydroxy-5H-dibenz[b,f]azepine-5-carboxamide with (2S,3S)-di-O,O'-substituted-tartaric acid anhydride to give a separable mixture (1:1) of diastereoisomeric 10-O-di-O,O'-substituted-tartrate half-esters of (±)-10,11-dihydro-10-hydroxy-5H-dibenz[b,f]azepine-5-carboxamide;

(2) precipitation of the less soluble diastereoisomeric 10-O-di-O,O'-substituted-tartrate half-ester formed in step (1) by addition of water and separation of the same by filtration;

(3) base-catalysed hydrolysis of the less soluble diastereoisomeric 10-O-di-O,O'-substituted-tartrate half-ester obtained in step (2) to give the optically pure (R)-(−)-10,11-dihydro-10-hydroxy-5H-dibenz[b,f]azepine-5-carboxamide;

(4) recovery from the organic filtrate from step (2) of the more-soluble diastereoisomeric 10-O-di-O,O'-substituted-tartrate half-ester;

(5) base-catalysed hydrolysis of the recovered, more-soluble diastereoisomeric 10-O-di-O,O'-substituted-tartrate half-ester from step (4) to give enriched (S)-(+)-10,11-dihydro-10-hydroxy-5H-dibenz[b,f]azepine-5-carboxamide;

(6) reaction of enriched (S)-(+)-10,11-dihydro-10-hydroxy-5H-dibenz[b,f]azepine-5-carboxamide from step (5) with (2R,3R)-di-O,O'-substituted-tartaric acid anhydride to give a separable mixture of diastereoisomeric 10-O-di-O,O'-substituted-tartrate half-esters;

(7) precipitation of the less soluble diastereoisomeric 10-O-di-O,O'-substituted-tartrate half-ester formed in step (6) by addition of water and separation of the same by filtration; and (8) base-catalysed hydrolysis of the less soluble 10-O-di-O,O'-substituted-tartrate half-ester obtained in step (7) to give the optically pure (S)-(+)-10,11-dihydro-10-hydroxy-5H-dibenz[b,f]azepine-5-carboxamide, wherein the (2R,3R)-di-O,O'-substituted-tartaric acid anhydride has the formula:

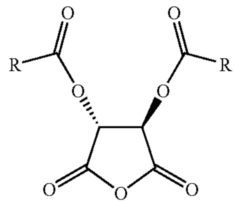

where each R is the same and is $C_1$ to $C_6$ alkyl, or each R is phenyl, and wherein the (2S,3S)-di-O,O'-substituted-tartaric acid anhydride has the formula:

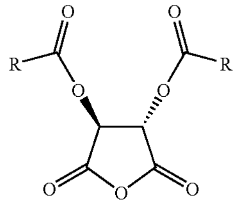

where each R is the same and is $C_1$ to $C_6$ alkyl, or each R is phenyl.

5. The method according to claim 1, wherein the (2R,3R)-di-O,O'-substituted-tartaric acid anhydride is (2R,3R)-di-O,O'-acetyltartaric acid anhydride or (2R,3R)-di-O,O'-benzoyltartaric acid anhydride.

6. The method according to claim 2, wherein the (2S,3S)-di-O,O'-substituted-tartaric acid anhydride is (2S,3S)-di-O,O'-acetyltartaric acid anhydride or (2S,3S)-di-O,O'-benzoyltartaric acid anhydride.

7. The method according to claim 1, wherein step (1) is effected in dichloromethane in the presence of pyridine.

8. The method according to claim 1, wherein the base used for step (3) is aqueous sodium hydroxide.

9. A method for the preparation of a compound of the formula III:

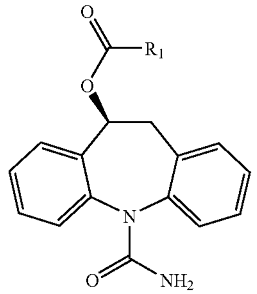

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 18 carbon atoms; the term halogen means fluorine, chlorine, bromin or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming (S)-(+)-10,11-dihydro-10-hydroxy-5H-dibenz[b,f]azepine-5-carboxamide by the method according to claim 1, then treating the (S)-(+)-10,11-dihydro-10-hydroxy-5H-dibenz[b,f]azepine-5-carboxamide to produce the compound of formula III.

10. The method according to claim 9, wherein the compound of formula III is prepared by acylating the (S)-(+)-10,11-dihydro-10-hydroxy-5H-dibenz[b,f]azepine-5-carboxamide.

11. A method of preparing (S)-(+)-10-acetoxy-10,11-dihydro-5H-dibenz[b,f]azepine-5-carboxamide comprising forming (S)-(+)-10,11-dihydro-10-hydroxy-5H-dibenz[b,f]azepine-5-carboxamide by the method according to claim 1, then acylating the (S)-(+) -10,11-dihydro-10-hydroxy-5H-dibenz[b,f]azepine-5-carboxamide with acetylchloride.

12. A method for the preparation of a compound of the formula IV:

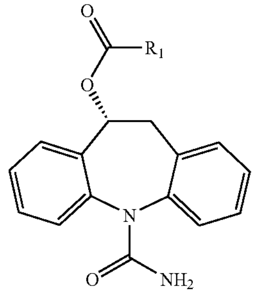

where $R_1$ is hydrogen, alkyl, halogenalkyl, aralkyl, cycloalkyl, cycloalkylalkyl, alkoxy, aryl, or pyridyl; the term alkyl means a straight or branched hydrocarbon chain containing from 1 to 8 carbon atoms; the term halogen means fluorine, chlorine, bromin or iodine; the term cycloalkyl means an alicyclic saturated group with 3 to 6 carbon atoms; and the term aryl means an unsubstituted phenyl group or phenyl substituted by alkoxy, halogen or nitro group, said method comprising forming (R)-(−)-10,11-dihydro-10-hydroxy-5H-dibenz[b,f]azepine-5-carboxamide by the method according to claim 2, then treating the (R)-(−)-10,11-dihydro-10-hydroxy-5H-dibenz[b,f]azepine-5-carboxamide to produce the compound of formula IV.

13. The method according to claim 12, wherein the compound of formula IV is prepared by acylating the (R)-(−)-10,11-dihydro-10-hydroxy-5H -dibenz[b,f]azepine-5-carboxamide.

14. A method of preparing (R)-(−)-10-acetoxy-10,11-dihydro-5H -dibenz[b,f]azepine-5-carboxamide comprising forming (R)-(−)-10,11-dihydro-10-hydroxy-5H -dibenz[b,f]azepine-5-carboxamide by the method according to claim 2, then acylating the (R)-(−)-10,11-dihydro-10-hydroxy-5H-dibenz[b,f]azepine-5-carboxamide with acetylchloride.

15. A compound of formula V:

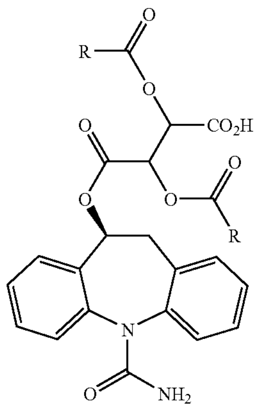

where each R is a $C_1$ to $C_6$ alkyl, or each R is phenyl.

16. The compound according to claim 15, wherein each R is methyl.

17. A compound of formula VI:

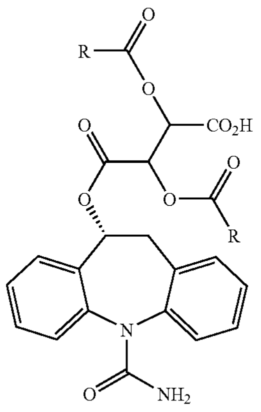

where each R is a $C_1$ to $C_6$ alkyl, or each R is phenyl.

18. The compound according to claim 17, wherein each R is methyl.

19. The method according to claim 2, wherein step (1) is effected in dichloromethane in the presence of pyridine.

20. The method according to claim 2, wherein the base used for step (3) is aqueous sodium hydroxide.

* * * * *